United States Patent [19]

Bauer et al.

[11] Patent Number: 5,258,185
[45] Date of Patent: Nov. 2, 1993

[54] HIGHLY ACTIVE, RAPIDLY ABSORBABLE FORMULATIONS OF GLIBENCLAMIDE, PROCESSES FOR THE PRODUCTION THEREOF AND THEIR USE

[76] Inventors: Kurt H. Bauer, Im Finkeler 4, D-7800 Freiburg-Tiengen; Manfred Keller, Hegegasse 7, 7812 Bad Krozingen, both of Fed. Rep. of Germany

[21] Appl. No.: 746,540

[22] Filed: Aug. 19, 1991

Related U.S. Application Data

[63] Continuation-in-part of Ser. No. 570,559, Aug. 21, 1990, abandoned.

[30] Foreign Application Priority Data

Aug. 23, 1989 [DE] Fed. Rep. of Germany ....... 3927882

[51] Int. Cl.$^5$ ............ A61K 47/10; A61K 47/26; A61K 9/08; A61K 9/14
[52] U.S. Cl. .................. 424/484; 424/439; 424/452; 424/465; 424/451; 424/464; 424/474; 424/489; 424/499; 424/488; 514/866; 514/960
[58] Field of Search ............... 424/456, 452, 465–466, 424/474, 484; 514/866, 941, 960, 962

[56] References Cited

U.S. PATENT DOCUMENTS

| | | | |
|---|---|---|---|
| 3,979,520 | 9/1976 | Rothe et al. | 424/321 |
| 4,696,815 | 9/1987 | Schepky et al. | 424/80 |
| 4,708,868 | 11/1987 | Brickl et al. | 424/80 |
| 4,727,109 | 2/1988 | Schmidt et al. | 424/455 |

FOREIGN PATENT DOCUMENTS

0086468 11/1983 European Pat. Off.
0128482 6/1984 European Pat. Off.
3228384 7/1982 Fed. Rep. of Germany.

OTHER PUBLICATIONS

Martindale, 28th Ed., No. 14038-q, "Isomalt".
*ERSTE Internationale ZL-Qualitatsvergleichstudie*, "Erhebliche Qualitätsunterschiede bei Glibenclamide-Arzneimitteln", Apotheker Zeitung Nr. 50, Dec. 9, 1991 (with translation).
Blume, Henning et al., "Untersuchungen Zur Therapeutischen Relevanz Der Bioäquivalenz . . . Glibenclamidhaltiger Fertigarzneimittel", Pharmazeutiache Zeitung, 132, Jahrgang Nr. 39-24, Sep. 1987, p. 2352/101.
H. Schiweck, "Alimenta 19", p. 15 (1980).

*Primary Examiner*—Thurman K. Page
*Assistant Examiner*—Edward J. Webman
*Attorney, Agent, or Firm*—Sughrue, Mion, Zinn, Macpeak & Seas

[57] ABSTRACT

This invention relates to highly active and solid pharmaceutical preparations rapidly releasing the active substance for the treatment of diabetes, particularly: 1. liquid formulations of glibenclamide consisting of 1 part of glibenclamide and 4 to 1500 parts of liquid sugar alcohols such as 70% sorbitol solution or glycol such as propylene glycol, hexylene glycol, di-, tri- or polyethylene glycol having a molecular weight from 76 to 600, optionally 0.5 to 2 moles of an alkaline reacting substance and other drug additives; 2. solid formulations of glibenclamide consisting of 1 part of glibenclamide, 4 to 30 parts of sugar alcohols, preferably 70% sorbitol solution, optionally dilute in alcohol, 30 to 150 parts of pharmacologically safe excipients, carrier mterials or other drug additives; and this invention also relates to a process for the production of a molecularly disperse solution or active substance alloy of glibenclamide or another sparingly soluble substance selected from the group consisting of sulfonyl ureas or substances and/or compounds having similar chemico-physical properties.

20 Claims, No Drawings

HIGHLY ACTIVE, RAPIDLY ABSORBABLE FORMULATIONS OF GLIBENCLAMIDE, PROCESSES FOR THE PRODUCTION THEREOF AND THEIR USE

This is a continuation-in-part of application Ser. No. 07/570,559 filed Aug. 21, 1990, now abandoned.

INTRODUCTION

Glibenclamide (INN) is a sulfonyl urea derivative having the chemical IUPAC designation: N-4-(5-chloro-[2-methoxy-benzamido)ethyl]phenylisulfonyl-N'-cyclohexyl urea. Glibenclamide is an odorless white crystalline substance virtually insoluble in water and ether and only moderately soluble in alcohol and chloroform. Together with alkalis, it forms salts which, have very limited solubility in water as compared to tolbutamide, which is also a blood sugar reducing substance. The molecular weight is 494.02, and the melting point is 172° to 174° C. (cf. R. Gröning: Arzneistoffprofile und Bioverfügbarkeitsdaten von Fertigarzneimitteln, Arzneistoffmonographie Glibenclamid, Deutscher Apothekerverlag, Stuttgart, pages 1 to 7, 1987; Euglucon® N, Semi-Euglucon® N: Pharmakologische und klinische Daten, Präparateinformation Boehringer Mannheim GmbH und Hoechst AG, Frankfurt/Main, 1984).

Glibenclamide has blood sugar reducing properties, and today it is used on a broad basis for the treatment of diabetes (diabetes mellitus) world-wide. The blood sugar reduction caused by glibenclamide is due to two mechanisms, i.e. a pancreatic effect and an extrapancreatic effect (cf. the above-mentioned publication of Boehringer Mannheim and Hoechst AG).

The pancreatic effect leads to a rise in insulin secretion caused by an increased responsiveness of the beta cells in the pancreas to glucose.

In the case of insulin resistance, the extrapancreatic effect is indicated by an increase of insulin activity resulting from:
- increase of insulin susceptibility and insulin binding of the target tissue:
- direct effect on the insulin receptors with respect to reproduction.

Due to the high rate of effectiveness and tolerance of glibenclamide, these preparations are currently of utmost importance for the oral treatment of diabetes.

State Of The Art And Requirements For An Optimum Drug Formulation

As is well known and proven by investigations, not only is the glibenclamide active substance of major importance for obtaining a therapeutic effect, but the same applies to its pharmaceutico-technological formulation, also referred to as galenical (cf. H. Blume et al.: Zur Bioverfügbarkeit und pharmakodynamischen Aktivität handelsüblicher Glibenclamid-Fertigarzneimittel, 1. Mitteilung: Bioequivalenzprüfung an gesunden Probanden unter oraler Kohlenhydratbelastung: Pharm. Ztg., 130, 10621069, 1985;

2. Mitteilung: Untersuchungen der glibenclamidinduzierten Veränderungen der Insulinkonzentration im Serum und der Blutglucosewerte an gesunden Probanden. Pharm. Ztg., 130, 1070–1078, 1985;

3. Mitteilung: Bioequivalenzprüfung an gesunden Probanden unter Dauerinfusion von Glucoselösung. Pharm. Ztg., 130, 2606–2610, 1985).

It follows from these investigations that due to its minor water-solubility and dissolution rate that glibenclamide is counted among the biopharmaceutically problematic pharmaceutical preparations. Furthermore, water solubility depends on the pH value; in the acidic range, glibenclamide is virtually water-insoluble.

As is also known, the dissolution rate depends on the particle size and/or the expansion of the particle surface (cf. H. Borchert et al.: Zur pharmazeutischen Qualität von Glibenclamid in Abhägigkeit von der Teilchengröße, Pharmazie, 31, 307–309, 1976). Years ago, efforts were already being made to improve the poor solubility and dissolution rate of glibenclamide.

It was found that preparations having micronized, i.e. finely comminuted, glibenclamide (mean particle size±5 μm) showed an improved drug release and bioavailability above all in the presence of tensides (cf. R. Gröning, cited above, H. Borchert et al., cited above.

DE-OS 23 48 334 describes a rapidly absorbable formulation of glibenclamide and a process for the production thereof. Glibenclamide was processed into rapidly absorbable formulations by means of pulverization to form as large a surface finest as possible or by finest precipitation, from organic solvents in dispersing agents. Extremely fine crystallizates having a surface size of 3 to 10 m$^2$ were obtained by the methods defined in DE-OS 23 48 334. Investigations showed that an increase in surface results in an increase in solubility and dissolution rate, thereby improving the bioavailability as well.

One glibenclamide tablet (Semi-Euglocun® N) with an active component content of 1.75 mg served to obtain active component levels of glibenclamide the same as a tablet containing 2.5 mg of glibenclamide (Euglucon® 2.5). In this case, no differences existed with respect to maximum serum concentrations ($C_{max}$ about 100 ng/ml for both formulations), whereas $T_{max}$ (about 1 hour) was reached about 1.5 hours earlier than with the former formulation Semi-Euglucon® 2.5 Thus, from these investigations and comparative studies on the exchangeability of glibenclamide-containing finished pharmaceutical preparations, it follows that, as determined by the grain and/or surface size, the solubility of glibenclamide is of major importance for the bioavailability and effectiveness of the various preparations and that certain preparations are not suitable for substitution (cf. H. Blume et al.: Untersuchungen zur therapeutischen Relevanz und zur Chargenhomogenität glibenclamidhaltiger Fertigarzneimittel, Pharm. Ztg., 132, 2352–2362, 1987).

Furthermore, it is well known that in the production of dosage forms that temperature load may affect the stability of the active substance. DE-OS 23 55 743 gives examples showing that processing glibenclamide at elevated temperatures, e.g. by incorporation in melts of high molecular polyethylene glycols, is detrimental to stability.

Furthermore, it has recently been discussed to what extent polyethylene glycols might possibly release ethylene oxide suspected of causing cancer, particularly when exposed to temperature load. According to an empirical principle of chemico-physical chemistry, it is known that a temperature increase of 10° C. results in a reaction rate which is about twice as fast. The temperature should therefore be kept as low as possible during the production process. In this connection, it becomes apparent why some regulatory health authorities, e.g., the German Federal Board of Health, require pharmaceutical manufacturers to prove that polyethylene glycols used for finished pharmaceutical products do not contain over 1 ppm of ethylene oxide.

Only few commercial preparations, such as Euglucon® N tablets, have a relatively rapid drug release for glibenclamide in vitro and therefore a sufficiently rapid and good absorption and/or bioavailability in vivo. Rapid absorption of the active substance from the formulation offers the following advantages:

1. Due to patients' behavior with respect to taking drugs, the formulation may simultaneously be administered with food.
2. The active substance, accurately adjusted, is available in vivo in the amount required and in time, thereby preventing the occurrence of increased or considerably varying blood sugar values.
3. Hyperglycemias resulting from food intake or other influences can be prevented or rapidly normalized.

Formulations not meeting these requirements for rapid drug release will involve the danger of hyperglycemias if no sufficient amount of active substance is available for absorption on account of insufficient solubility and/or release. However, a precondition for rapid absorption is that the active substance of the formulation is available for release, if possible, in a dissolved or colloidally dissolved or molecularly dispersely distributed form. The active substance can be rapidly absorbed, thereby becoming active, only if these conditions are met.

Object Of The Invention

The object of the present invention was to develop highly active, rapidly absorbable formulations of sparingly soluble, blood sugar reducing sulfonyl urea derivatives such as glibenclamide and to provide processes for the production thereof.

The sparingly soluble active substance glibenclamide should be put into solution, if possible, in a molecularly disperse form by means of a simple process and pharmacologically, toxicologically safe excipients. The active substance is pulverized and has good solubility due to its large surface. For the purpose of surface expansion, the molecularly dispersely distributed active substance may be adsorbed onto or absorbed into conventional pharmaceutical carrier materials so as to obtain an active substance-excipient alloy. The molecularly disperse dissolution enables rapid absorption of sparingly soluble sulfonyl urea derivatives such as glibenclamide from the gastrointestinal tract. In order to avoid hyperglycemias, glibenclamide is immediately available when needed or in connection with food intake (e.g. by carbohydrate supply).

It should be possible to carry out the process for the production of the formulations according to the invention in a technically simple manner. No expensive apparatuses and no complex process steps should be necessary. In addition, this process should guarantee mild treatment of the active substance, e.g. at low temperatures and not negatively affect its stability. Production should be possible with commercially available pharmacopeial excipients and simple manufacturing means, and the production process should not negatively affect the chemico-physical properties of active substances and/or excipients.

Subject Matter Of The Invention

In contrast to the water-soluble carrier substances defined in DE-OS 23 55 743, which require a melting point above 50° C., it was surprisingly found that low-molecular polyethylene glycols can dissolve glibenclamide better. Another advantage is that the external heat supply can thereby be kept at temperatures below 50° C. Thus, low-molecular polyethylene glycols can reduce or avoid possible stability impairment of glibenclamide.

Surprisingly it has now been found that the amount of polyethylene glycol necessary according to Examples 1 and 2 of DE-OS 23 55 743 can be lowered up to ten times the amount if 0.5 to 3 moles, preferably 1 mole, of ammonia, concentrated (35%) or dilute in ethanol (10%), is added to the glibenclamidepolyethylene-glycol mixture.

Surprisingly, it has further been found, that the amount of glycols and polyethylene glycols, usually necessary to prepare relatively high concentrated solutions of GLIBENCLAMIDE with an alkaline oxide or hydroxide or ammonia, could be considerably reduced respectively, if not completely eliminated, if the GLIBENCLAMIDE was previously wetted with a sufficient amount of a lower aliphatic alcohol, and the wetted glibenclamide is then dissolved by a highly concentrated aqueous solution of a sugar alcohol. The sugar alcohol must be extremely soluble in water, at least 40% or more, e.g., a 70% sorbitol solution or a 50% or 60% xylitol solution. As lower aliphatic alcohols, for instance, methanol, ethanol, n-propanol or isopropanol can be used.

The production process according to the invention must be performed in the following sequence.

The first step is wetting the GLIBENCLAMIDE with a sufficient amount of a lower aliphatic alcohol. Then the highly concentrated aqueous solution of a sugar alcohol is added by vigorous stirring, and finally an equimolecular amount of the GLIBENCLAMIDE of aqueous ammonia or alkaline oxide or hydroxide is added.

For prepared the basic solution according to the invention, the following compositions are possible and useful:

|  | preferably: (in parts) | more extended |
|---|---|---|
| Glibenclamide | 1 |  |
| Ethanol* | 2–6 | (1–20) |
| Sorbitol-solution 70%** | 3–15 | (2–20) |
| 1 N—NH₃ aqueous solution*** | 2 |  |
| Water | 1–20 | (1–▽) |

*or another lower aliphatic alcohol
**or a highly concentrated solution of another sugar alcohol
***or 1 N NaOH-solution This concentrated GLIBENCLAMIDE solution produced according to this invention is in principle a basic solution to make liquid as well as solid dosage forms.

To make liquid dosage forms, it must be diluted with water, water-alcohol or water-glycol or polyethylene glycol mixtures in order to get the optimal concentration with respect to the desirable or prescribed dose of GLIBENCLAMIDE for drop solutions or other peroral liquids, depending on whether they are to be applied dropwise or with a teaspoon.

For the production of solid dosage forms, e.g., granules, pellets, tablets, coated tablets or capsules, usual and known ingredients for solid dosage form, for instance, lactose cellulose powder, microcrystalline cellulose, mannitol, starches, calcium carbonate, calcium diphosphate, calcium sulfate, and the like, alone or mixtures thereof, must be wetted homogeneously with the basic GLIBENCLAMIDE solution by vigorous mixing, and finally dried. By this method, the chosen ingredients for solid dosage forms, or mixtures thereof, are homogeneously coated with the basic solution, and, after drying, the GLIBENCLAMIDE remains in a fine dispersion, essentially a molecular dispersion embedded within the sugar alcohol, as a solid solution or alloy, on the surfaces of the solid ingredients. From this solid solution it is released rapidly and essentially to completion.

The invention therefore, relates to processes for the production of rapidly releasing, optimally absorbable, and therefore highly effective liquid and solid medicaments.

Forms of administration containing GLIBENCLAMIDE in the formulations according to the present invention offer great advantages because they can be administered together with the food or directly after food intake, for example, during or after breakfast. Tablets prepared in this way show in the in vitro dissolution test (Paddle apparatus according to USP XXII, 75 r.p.m. rounds per minute, buffer pH 7.4, U.V. measurement at 227 nm) a 100% drug release within 5 to 15 minutes. Due to the rapid dissolution of GLIBENCLAMIDE in molecularly dispersed or colloidal form, the active substance can be rapidly absorbed. Blume et al (Ph. Ztg. 132, 39, 2352/101-2362/111, 1987) has shown in comparative in vitro/in vivo investigations that the bio-availability and effect directly depend on the dissolution rate of the active substance and the active substance is available the faster and more rapidly it is released in vitro. With respect to Euglucon N tablets having an in vitro dissolution of 100% after 15 minutes, an average age of $T_{max}$ of less than 1.5 h and $C_{max}$ of more than 150 ng/ml×h was achieved in 12 patients. In the case of 3 charges of the generic preparation Glyoklande N, the corresponding pharmacokinetic parameters disseminate with in vitro dissolution rates of less than 80% within 30 minutes for $T_{max}$ of 2.3 to 3.3 h and for $C_{max}$ of 120 to 133 ng/ml×h.

With respect to practical application, this means that the molecularly dispersely dissolved GLIBENCLAMIDE according to the invention has an optimum bio-availability in the form of both drops and tablets because the active substance is fully available for absorption and thus, becoming effective directly after the administration and from the tablets within 5 to 15 minutes.

Production Process

The process of production of liquid GLIBENCLAMIDE formulation is very easy and can be performed in a stainless steel vessel with stirring equipment.

1 part of GLIBENCLAMIDE is wetted in 5-50 parts of aliphatic alcohol, like ethanol 95% under vigorous stirring. After receiving a homogenous suspension, 5-150 parts of sorbitol solution (70% in water) or xylitol solution (40% in water) are added. A clear solution can be achieved by adding an equimolar amount or little excess of alkaline reacting substance, like 1 N—NaOH. The resulting solution can be diluted with water to a therapeutic concentration of about 0.5-10 mg GLIBENCLAMIDE per 1g of solution. For oral application, usually sweeteners like aspartame, saccharine sodium, and the like, flavoring substances, like orange-, raspberry-, strawberry- or other suitable fruit flavors and preservatives like esters of para-hydroxybenzoic acid, benzylic alcohol, and the like are added in concentrations of 0.1 up to 1%.

Another way of production for the present invention is to suspend 1 part of GLIBENCLAMIDE directly in 150-300 parts of propyleneglycol, glycerol, hexyleneglycol or polyethyleneglycol having a molecular weight of 200-600. After adding an equimolar amount or little excess of alkaline reacting substance, like 1 N—NaOH, the solution can be diluted with water containing sweeteners, flavors, and preservatives like above to a therapeutic concentration of about 0.5-10 mg GLIBENCLAMIDE per 1 g of solution.

For the production of solid application forms, first a concentrated GLIBENCLAMIDE solution containing 1 part of GLIBENCLAMIDE dissolved in 2-6 parts aliphatic alcohol, like ethanol 95%, 3-15 parts of sorbitol solution (70% in water) and an equimolar concentration or slight excess of alkaline substance in respect to GLIBENCLAMIDE, like 0.1-0.5 N $NH_3$-solution in water, will be prepared as above. This solution is adsorbed onto on pharmaceutically common tabletting excipients in a conventional mixing vessel or fluid-bed granulator. It is preferred to adsorb the solution in a finely disperse manner on starches, mannitol, palatinitol, lactose, cellulose, microcrystalline cellulose, cellulose ethers, calcium carbonate, calcium diphosphate, calcium ..sulfate, dispersing and disintegrating agents, and the like, alone or mixtures thereof. Excessive alcohol, ammonia or also water may be removed in a drying oven.

By such a procedure, the active substance is distributed quasi-molecularly disperse or as an active substance alloy on a large surface, releasing GLIBENCLAMIDE to 100% very rapidly within 5 to 15 minutes in a concentration 1 to 5 mg per single solid application dose.

Examples 1. 1 part of GLIBENCLAMIDE is mixed in 200 parts of propyleneglycol. 1N-NaOH solution will be added until a clear solution results. This solution will be diluted with water to 350 parts.

2. part of GLIBENCLAMIDE is suspended in 150 g of polyethyleneglycol 200. 0.1 N ammonia solution is added until a clear solution results. 0.2% parabens and aspartame dissolved in 100 ml of water will be added to the solution.

3. 1 part GLIBENCLAMIDE is suspended in 20 parts of ethanol 95%. 100 parts of a xylitol solution (40% in water) will be added under stirring, finally 1N-NaOH solution will be added until a clear solution results. The solution will be diluted in 250 parts with water containing parabens, saccharine sodium and flavoring substances in a concentration of 0.2% respectively.

4. 10 g of GLIBENCLAMIDE are suspended in 60 g of isopropanol, mixed with 40 g of 70% sorbitol solution and 1 N ammonia solution is added until a clear solution is obtained. This solution is then attached to a mixture consisting of 50 g of microcrystalline cellulose, 50 g of lactose and 100 g of corn starch and 25 g of blasting agent and compressed after drying by adding 1% of magnesium stearate and silicon dioxide each.

5. 5 g of GLIBENCLAMIDE are suspended in 12 g of ethanol and 50 g of Karion F (70% sorbitol solution), mixed with 10 g of 1 N sodium hydroxide solution and diluted with 360 g of water.

6. 5 g of GLIBENCLAMIDE is initially suspended in 200 g of ethanol and then 100 g of 70% sorbitol solution. After the addition of 20 g of 0.5 N sodium hydroxide solution, a clear solution is obtained.

7. 10 g of GLIBENCLAMIDE are suspended in 50 g of ethanol and 50 g of 70% sorbitol solution and 2.5% ammonia solution, is added until a clear solution results. This solution is mixed with 120 g of corn starch and then ground with 120 g of lactose. After drying and screening, the granulate is mixed with 50 g of a tabletting excipient mixture and then compressed into tablets.

What is claimed:

1. A liquid formulation of glibenclamide consisting essentially of a solution of 1 part of glibenclamide, 2 to 60 parts of an aliphatic alcohol or mixtures thereof, and 3 to 140 parts of at least one sugar alcohol having a water solubility of at least 40% wherein said sugar alcohol is dissolved in 10 to 200 parts of water, and 0.5 to 2 moles of an alkaline reacting substance selected from the group consisting of alkali hydroxides, alkaline earth hydroxides, alkaline oxides and ammonia, based upon moles glibenclamide, and optionally other pharmaceutically common excipients selected from the group consisting of flavoring agents, buffer substances and preservatives in a total concentration of 0.1 to 2% by weight, based on the liquid formulation.

2. A liquid formulation of glibenclamide comprising a solution of 1 part of glibenclamide, 100 to 500 parts of a compound selected from the group consisting of glycerol, propylene glycol, hexylene glycol, and mixtures thereof, and 0.5 to 2 moles of an alkaline reacting substance selected from the group consisting of alkali hydroxides, alkaline earth hydroxides, alkaline oxides and ammonia, based upon moles glibenclamide, and optionally other pharmaceutically common excipients selected from the group consisting of sugar alcohols in a concentration of 1 to 20%, flavoring agents, buffer substances and preservatives in a total concentration of 0.1 to 2% by weight, based on the liquid formulation.

3. A solid formulation of glibenclamide consisting essentially of a solution of 1 part of glibenclamide, 2 to 30 parts of an aliphatic alcohol or mixtures thereof, and 3 to 70 parts of at least one sugar alcohol having a water solubility of at least 40% wherein said sugar alcohol is dissolved in 10 to 100 parts of water, and 0.5 to 2 moles of an alkaline reacting substance selected from the group consisting of alkali hydroxides, alkaline earth hydroxides, alkaline oxides and ammonia based upon moles glibenclamide, dispersed on 20 to 400 parts of a pharmaceutically acceptable solid excipient.

4. A formulation according to claim 3, further comprising silicon dioxide and magnesium stearate, and wherein said pharmaceutically solid excipient is selected from the group consisting of starches, mannitol, lactose, sorbitol, xylitol, isomalt, cellulose, microcrystalline cellulose, cellulose ethers, calcium carbonate, calcium diphosphate, calcium sulfate, croscarmellose, sodium bicarbonate, and mixtures thereof.

5. A liquid formulation according to claim 1, wherein said sugar alcohol comprises a sugar alcohol having a water solubility of 40 to 70%.

6. A liquid formulation according to claim 1, wherein said sugar alcohol is selected from the group consisting of sorbitol, xylitol, and isomalt, and mixtures thereof.

7. A liquid formulation according to claim 1, wherein said sugar alcohol is a 70% by weight sorbitol solution.

8. A liquid formulation according to claim 1, comprising an aliphatic alcohol selected from the group consisting of methanol, isopropanol, n-propanol and ethanol.

9. A formulation according to claim 1, comprising: a sweetener selected from the group consisting of aspartame and saccharine sodium; a fruit flavoring agent; and a preservative selected from the group consisting of an ester of a parahydroxybenzoic acid, benzylic alcohol, and sorbic acid, and salts thereof; in a combined concentration of 0.1 to 1% by weight based on the total formulation weight.

10. A formulation according to claim 1, wherein said formulation comprises an absorbable pharmaceutical dosage form selected from the group consisting of solutions, drops, juices, injections, and infusion solutions.

11. A formulation according to claim 10, wherein said dosage form comprises a final glibenclamide concentration of 0.5 to 5 mg glibenclamide for one application dose.

12. A liquid formulation according to claim 11, characterized in that sugar alcohols having a water solubility of 40 to 70% are used.

13. A process for the production of a liquid formulation according to claim 1, characterized in that glibenclamide is wetted under vigorous stirring with the aliphatic alcohol, then suspended in an aqueous solution of sugar alcohol and solubilized by adding the alkaline reacting substance.

14. A process according to claim 13, wherein said sugar alcohols are selected from the group consisting of sorbitol, xylitol, and isomalt, and mixtures thereof.

15. The process according to claim 14, characterized in that said sugar alcohol comprises a 70% by weight sorbitol solution.

16. A method for treating Diabetes mellitus in humans, which comprises administering a formulation as in claim 3.

17. A method for treating Diabetes mellitus in humans, which comprises administering a formulation as in claim 1.

18. A formulation as in claim 3, wherein said aliphatic alcohol is selected from the group consisting of methanol, ethanol, isopropanol and n-propanol.

19. A formulation as in claim 1, wherein 1 mole of alkaline reacting substance is contained.

20. A formulation as in claim 1, wherein said alkaline reacting substance is used in an excess of 10 to 20% by weight over the amount needed to solubilize the glibenclamide.

* * * * *